United States Patent
Dai et al.

(10) Patent No.: US 10,561,833 B2
(45) Date of Patent: Feb. 18, 2020

(54) CONDUCTIVE PAD FOR PAIN RELIEVING AND MUSCLE TRAINING

(71) Applicant: JKH Health Co., Ltd., Shenzhen (CN)

(72) Inventors: Quanqin Dai, Diamond Bar, CA (US); Pu Jiang, Shenzhen (CN)

(73) Assignees: Quanqin Dai, Diamond Bar, CA (US); Pu Jiang, Shenzhen (CN)

( * ) Notice: Subject to any disclaimer, the term of this patent is extended or adjusted under 35 U.S.C. 154(b) by 236 days.

(21) Appl. No.: 15/832,932

(22) Filed: Dec. 6, 2017

(65) Prior Publication Data
US 2018/0154131 A1    Jun. 7, 2018

(30) Foreign Application Priority Data
Dec. 7, 2016  (CN) .......................... 2016 1 11167144

(51) Int. Cl.
*A61N 1/04* (2006.01)
*A61N 1/36* (2006.01)

(52) U.S. Cl.
CPC ......... *A61N 1/0452* (2013.01); *A61N 1/0496* (2013.01); *A61N 1/36021* (2013.01); *A61N 1/0456* (2013.01); *A61N 1/36003* (2013.01); *A61N 1/36014* (2013.01)

(58) Field of Classification Search
CPC ................ A61N 1/0452; A61N 1/0456; A61N 1/36014; A61N 1/36021
See application file for complete search history.

(56) References Cited

U.S. PATENT DOCUMENTS

| | | | | |
|---|---|---|---|---|
| 8,569,935 | B1* | 10/2013 | Kosierkiewicz | H01L 41/047 310/339 |
| 2003/0023277 | A1* | 1/2003 | Owen | A61N 1/0452 607/5 |
| 2003/0032988 | A1* | 2/2003 | Fincke | A61N 1/0452 607/5 |
| 2008/0207985 | A1* | 8/2008 | Farone | A61N 1/36021 600/15 |
| 2010/0042180 | A1* | 2/2010 | Mueller | A61N 1/0456 607/46 |
| 2011/0213295 | A1* | 9/2011 | Henley | A61N 1/044 604/20 |

(Continued)

*Primary Examiner* — Christopher A Flory
(74) *Attorney, Agent, or Firm* — Karthik Murthy; Murthy Patent Law PLLC

(57) ABSTRACT

A conductive pad for pain relieving and muscle training, comprises an electrode sheet electrically connected to a control unit and a conductive gel for attaching onto the human body. The conductive gel is added with a substance for pain relieving and muscle training, which is capsaicin, menthol, lidocaine, or other substitutes in an amount of 0.001% to 30% by mass. This invention has the function of increasing the blood circulation/local anesthesia by adding capsaicin, menthol, lidocaine, or other substitutes to the conductive gel, and has the effect of pain relieving and muscle training. The conductive pad that is made of the above described conductive gel can be used alone, and also be used with all of the TENS/EMS units in the market, offering a wide range of application. In addition, this invention does not require the additional heating source, simplifies the structure, and greatly reduces the manufacturing costs.

18 Claims, 2 Drawing Sheets

(56) References Cited

U.S. PATENT DOCUMENTS

| | | | |
|---|---|---|---|
| 2012/0041296 A1* | 2/2012 | Garstka | A61B 5/04087 600/395 |
| 2012/0220975 A1* | 8/2012 | Chan | A61F 13/0206 604/384 |
| 2014/0065248 A1* | 3/2014 | Garstka | A61B 5/04087 424/744 |
| 2014/0276248 A1* | 9/2014 | Hall | A61N 1/0432 601/2 |
| 2014/0364918 A1* | 12/2014 | Owen | A61N 1/0452 607/6 |
| 2015/0151124 A1* | 6/2015 | Mueller | A61N 1/0456 607/46 |
| 2017/0080208 A1* | 3/2017 | Neuvonen | A61N 1/0404 |
| 2017/0095431 A1* | 4/2017 | Andrews | A61K 31/155 |
| 2018/0296831 A1* | 10/2018 | Matsushita | A61N 1/3603 |
| 2018/0326201 A1* | 11/2018 | Nagel | A61F 13/00051 |
| 2019/0083784 A1* | 3/2019 | Raghunathan | A61N 1/08 |
| 2019/0143097 A1* | 5/2019 | John | A61N 1/0456 607/149 |

* cited by examiner

CONDUCTIVE PAD FOR PAIN RELIEVING AND MUSCLE TRAINING

BACKGROUND

The existing TENS/EMS (TENS represents the physical therapy instrument that relieves pain; the EMS represents the muscle stimulator used for training and rehabilitation) unit usually transmits the stimulation from the control unit to the conductive pads attached to the body skin. In order to enhance the effectiveness of pain relieving and muscle training, the heating function is added to the conductive pad. The principle is the heat increases the blood circulation through the conductive pad attached to the body area. The addition of the heating function greatly increases the manufacturing cost of the conductive pad, and the cost for such a conductive pad is relatively high. In addition, in order to cooperate with the heating function, the conductive pad needs to be equipped with additional power supply, such as a large capacity battery and an AC adapter. This further increases the user's economic burden, and may not be good for the promotion and popularization of such a conductive pad with heat.

China Patent Document No. CN205672354U disclosed a stimulation and heating integrated physiotherapy instrument on Nov. 9, 2016, which specifically disclosed a control unit for providing a stimulation output, a power source for providing the heating energy, and a conductive pad comprising a heat generating sheet for heating and an electrode layer for stimulation. The heat generating element and the stimulation layer are fixed to the conductive pad. This structure has the above-mentioned high cost and complicated structure, and therefore, it may be necessary to make further improvement.

SUMMARY OF INVENTION

A conductive pad for pain relieving and muscle training, comprises an electrode sheet electrically connected to a control unit and a conductive gel for attaching onto the human body. The conductive gel is added with a substance for pain relieving and muscle training, which is capsaicin, menthol, lidocaine, or other substitutes in an amount of 0.001% to 30% by mass. This invention has the function of increasing the blood circulation by adding capsaicin, menthol, lidocaine, or other substitutes to the conductive gel, and has the effect of pain relieving and muscle training. The conductive pad that is made of the above described conductive gel can be used alone, and also be used with all of the TENS/EMS units in the market, offering a wide range of application. In addition, this invention does not require the additional heating source, simplifies the structure, and greatly reduces the manufacturing costs.

TECHNICAL FIELD

The present invention relates to a conductive pad for TENS/EMS, and more particularly to a conductive pad for pain relieving and muscle training.

DETAILED DESCRIPTION

Figure 1:
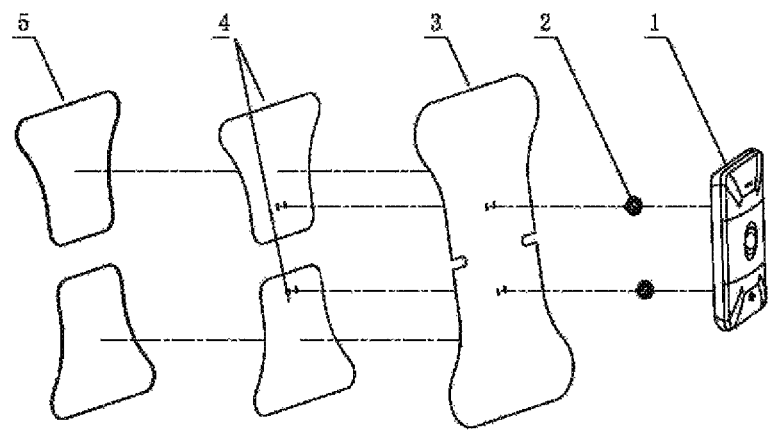
FIG. 1 is a view of a first embodiment of the present invention.

It is an object of the present invention to provide a conductive pad for pain relieving and muscle training, which is simple, reasonable, economical, effective, and wide application to overcome deficiencies in the prior art.

A conductive pad for pain relieving and muscle training, comprises an electrode sheet electrically connected to a control unit and a conductive gel for attaching onto the human body.

The conductive gel is in contact with the corresponding electrode sheet. The substances used for pain relieving and muscle training in the conductive gel are capsaicin, menthol, lidocaine, camphor, methyl salicylate, trolamine salicylate, *arnica montana, Calendula officinalis*, hypericum perforatum, symphytum *officinale*, or any combination of these substances, the mass fraction of which is from 0.001% to 30%.

The conductive gel also includes the following components: glycerol, water, polyols, chlorides and acrylic polymers. The conductive electrode sheet is provided with one or more pieces, and electrode sheets are insulated for use with the TENS/EMS unit.

The conductive pad further comprises a carrier, on which the conductive connector is located; the electrode sheet is electrically connected to the control unit through the conductive connector on the carrier. Alternatively, the conductive pad further comprises a carrier on which the conductive lead wire is connected; the electrode sheet is electrically connected to the control unit through a lead wire.

In addition, the electrode gel may be directly attached on the control unit.

Being added with capsaicin, menthol, lidocaine, camphor, methyl salicylate, trolamine salicylate, *arnica montana, Calendula officinalis*, hypericum perforatum, symphytum *officinale*, or any combination of these substances, the conductive gel has the function of increasing blood circulation, and enhances the effect of pain relieving and muscle training. With the conductive gel included, the conductive pad can not only be used alone, but also be used with all of the TENS/EMS units in the market. Therefore, the conductive pad shows a wide range of application. In addition, no need of the additional heating source simplifies the structure, and greatly reduce the manufacturing costs.

First Embodiment

The first embodiment of the present invention is used as a conductive pad for pain relieving and muscle training, comprising a carrier 3 for fixing two conductive connectors 2, two conductive electrode sheets 4, and two pieces of conductive gel 5 for attaching onto the body skin; the carrier 3, electrode sheet 4, and conductive gel 5 are sequentially attached; the conductive gel 5 is added with capsaicin, and the conductive gel 5 is in contact with the corresponding electrode sheet 4; the conductive gel 5 has a certain viscosity so it could be adhered to the human body. The conductive pad itself has the effectiveness of pain relieving and muscle training through the conductive gel 5, and is able to be used together with the TENS/EMS unit to enhance the effectiveness. In addition, it does not need the additional heating source, thus simplifying the structure and significantly reducing the cost.

Further, the conductive gel 5 comprises the following components: capsaicin, glycerol, water, polyol (e.g., propylene glycol), chlorides (e.g., potassium chloride) and acrylic polymers. Among them, the mass fraction of capsaicin is 0.025%. In the process of making conductive gel 5, it is necessary to carry out the steps of feeding, mixing and coating, which can be completed by automatic production line to ensure product quality and product consistency. Then the conductive gel 5 is attached to the electrode sheet and carrier, cut into a desired size/shape, and sealed in the bag for storage.

Further, the electrode sheet 4 is provided with two pieces, each of which is in contact with a corresponding conductive gel 5. The electrode sheets are insulated.

Further, the two electrode sheets 4 are attached on the carrier 3, and the carrier 3 is equipped with two conductive connectors 2 which are electrically connected to the electrode sheets 4. The two conductive connectors are electrically connected to the control unit 1. The connection between the conductive connector 2 and the control unit 1 includes the mechanical fastening, magnetic contact, plug, and the like.

The Second Embodiment

Figure 2:
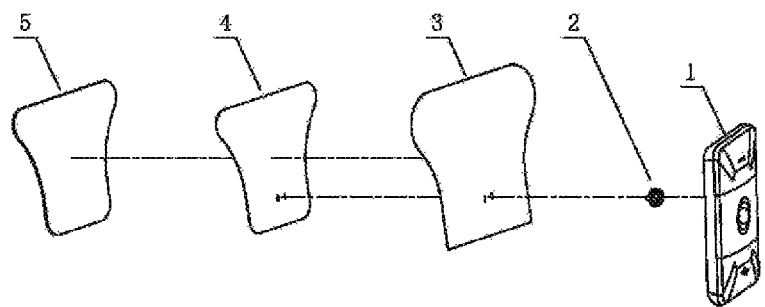
FIG. 2 is a view of a second embodiment of the present invention.

The second embodiment is referred to FIG. 2. Its difference from the first embodiment is as follows: The carrier 3 of each conductive pad is in contact with one electrode sheet 4, which is connected to one conductive connector 2. The conductive gel 5 is added with lidocaine (4%). Two pieces or an even number of pieces of such conductive pad are used together with the control unit.

The other parts of the second embodiment are the same as the first embodiment, and will not be described here.

The Third Embodiment

Figure 3:
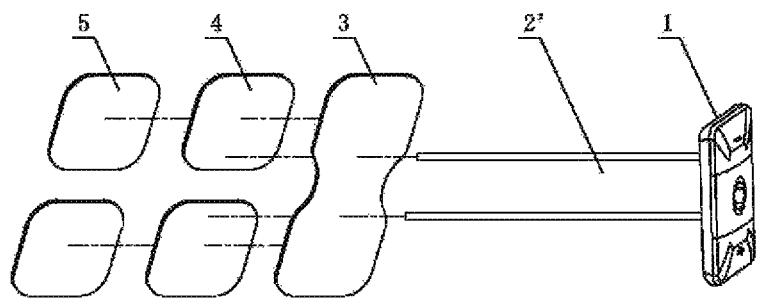
FIG. 3 is a view of a third embodiment of the present invention.

The third embodiment is referred to in FIG. 3. Its difference from the first embodiment is the control unit 1 is connected to the lead wire 2', and the electrode sheet 4 is electrically connected to the control unit 1 via a wire 2'.

The other parts of the third embodiment are described in the first embodiment, and thereof will not be described here.

The Fourth Embodiment

Figure 4:
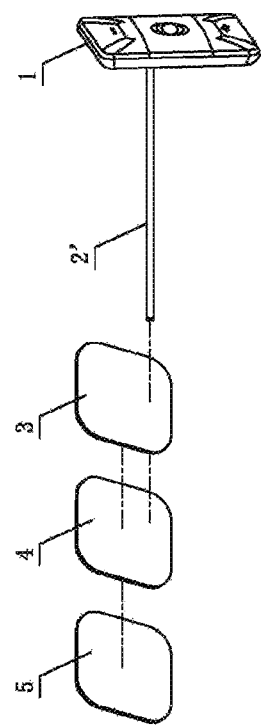
FIG. 4 is a view of a fourth embodiment of the present invention.

The fourth embodiment is referred to FIG. 4. Its difference from the first embodiment is that the carrier 3 is in contact with one electrode sheet 4, which is connected to one lead wire 2'. The electrode sheet 4 is electrically connected to the control unit 1 via the lead wire 2', and two pieces or an even number of pieces of the conductive pad in the fourth embodiment are used together with the control unit 1.

The other parts of the fourth embodiment are described in the first embodiment, and thereof will not be described here.

The Fifth Embodiment

Figure 5:
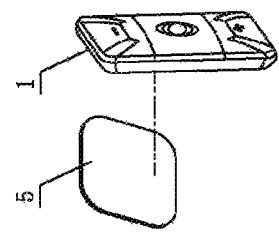
FIG. 5 is a view of a fifth embodiment of the present invention.

The fifth embodiment, is referred to FIG. 5. It differs from the first embodiment as follows: The carrier 3 is canceled; the electrode sheet 4 is provided with two pieces or an even number of pieces and is directly placed on the control unit 1; the conductive gel 5 is directly attached to the electrode sheet 4 on the control unit 1.

The other parts of the fifth embodiment are described in the first embodiment, and thereof will not be described here.

Having described the invention by the description and illustrations above, it should be understood that these are exemplary of the invention and are not to be considered as limiting. Accordingly, the invention is not to be considered as limited by the foregoing description, but includes any equivalents.

What is claimed is:

1. A conductive pad for pain relieving and muscle training, comprising an electrode sheet (4) electrically connected to a control unit (1) and a conductive gel (5) for attaching onto the human body; wherein the conductive gel (5) is added with a substance for pain relieving and muscle training, and the conductive gel (5) is in contact with the corresponding electrode sheet (4);

wherein a mass fraction of said substance for pain relieving and muscle training is 0.001% to 30%;

wherein said substance for pain relieving and muscle training is lidocaine, methyl salicylate, trolamine salicylate, *arnica montana, Calendula officinalis, hypericum* perforatum, symphytum *officinale*, or any combination of the said substances.

2. A conductive pad for pain relieving and muscle training according to claim 1, wherein the electrode sheet (4) is provided with one or more pieces, and electrode sheet (4) is insulated.

3. A conductive pad for pain relieving and muscle training according to claim 2, further comprising a carrier (3) on which a conductive connector (2) is located; the electrode sheet (4) is electrically connected to the control unit (1) through the conductive connector (2) on the carrier (3).

4. A conductive pad for pain relieving and muscle training according to claim 2, further comprising a carrier (3) on which a conductive lead wire (2') is connected; the electrode sheet (4) is electrically connected to the control unit (1) through a lead wire (2').

5. A conductive pad for pain relieving and muscle training according to claim 2, wherein the electrode sheet (4) is directly attached on the control unit (1).

6. A conductive pad for pain relieving and muscle training according to claim 1, further comprising:

wherein capsaicin is combined with one or more of the substances for pain relieving and muscle training;

wherein a mass fraction for capsaicin is 0.001% to 0.009%.

7. A conductive pad for pain relieving and muscle training according to claim 1, further comprising:

wherein capsaicin is combined with one or more of the substances for pain relieving and muscle training;

wherein a mass fraction for capsaicin is 1.001% to 30%.

8. A conductive pad for pain relieving and muscle training according to claim 1, further comprising:

wherein menthol is combined with one or more of the substances for pain relieving and muscle training;

wherein a mass fraction for menthol is 0.001% to 0.009%.

9. A conductive pad for pain relieving and muscle training according to claim 1, further comprising:

wherein menthol is combined with one or more of the substances for pain relieving and muscle training;

wherein a mass fraction for menthol is 20.001% to 30%.

10. A conductive pad for pain relieving and muscle training according to claim 1, further comprising:

wherein the electrode sheet (4) is provided with one or more pieces, and electrode sheet (4) is insulated;

a carrier (3) on which a conductive connector (2) is located;

wherein the electrode sheet (4) is electrically connected to the control unit (1) through the conductive connector (2) on the carrier (3).

11. A conductive pad for pain relieving and muscle training, comprising an electrode sheet (4) electrically connected to a control unit (1) and a conductive gel (5) for attaching onto the human body; wherein the conductive gel (5) is added with a substance for pain relieving and muscle training, and the conductive gel (5) is in contact with the corresponding electrode sheet (4);

wherein a mass fraction of said substance for pain relieving and muscle training is 0.001% to 30%;

wherein said substance for pain relieving and muscle training is a combination of capsaicin and menthol.

12. A conductive pad for pain relieving and muscle training according to claim 11, wherein the electrode sheet (4) is provided with one or more pieces, and electrode sheet (4) is insulated.

13. A conductive pad for pain relieving and muscle training according to claim 12, further comprising a carrier (3) on which a conductive connector (2) is located; the electrode sheet (4) is electrically connected to the control unit (1) through the conductive connector (2) on the carrier (3).

14. A conductive pad for pain relieving and muscle training, comprising an electrode sheet (4) electrically connected to a control unit (1) and a conductive gel (5) for attaching onto the human body; wherein the conductive gel (5) is added with a substance for pain relieving and muscle training, and the conductive gel (5) is in contact with the corresponding electrode sheet (4);

wherein a mass fraction of said substance for pain relieving and muscle training is 0.001% to 30%;

where said substance for pain relieving and muscle training is a combination of menthol and lidocaine.

15. A conductive pad for pain relieving and muscle training according to claim 14, wherein the electrode sheet (4) is provided with one or more pieces, and electrode sheet (4) is insulated.

16. A conductive pad for pain relieving and muscle training according to claim 15, further comprising a carrier (3) on which a conductive connector (2) is located; the electrode sheet (4) is electrically connected to the control unit (1) through the conductive connector (2) on the carrier (3).

17. A conductive pad for pain relieving and muscle training according to claim 15, further comprising a carrier (3) on which a conductive lead wire (2') is connected; the electrode sheet (4) is electrically connected to the control unit (1) through a lead wire (2').

18. A conductive pad for pain relieving and muscle training according to claim 15, wherein the electrode sheet (4) is directly attached on the control unit (1).

* * * * *